United States Patent [19]

Grollier et al.

[11] Patent Number: 4,710,374

[45] Date of Patent: Dec. 1, 1987

[54] COSMETIC COMPOSITION CONTAINING CATIONIC POLYMERS AND ANIONIC LATEXES

[75] Inventors: Jean F. Grollier, Paris; Claude Dubief, Versailles, both of France

[73] Assignee: L'Oreal, Paris, France

[21] Appl. No.: 467,185

[22] Filed: Feb. 16, 1983

[30] Foreign Application Priority Data

Feb. 16, 1982 [LU] Luxembourg .................... 83949

[51] Int. Cl.[4] .................... A61K 7/04; A61K 7/06; A61K 7/13; A45D 7/00
[52] U.S. Cl. .................... 424/61; 424/62; 424/70; 424/71; 424/72; 424/47; 424/DIG. 2; 514/846; 514/881; 132/7; 8/405
[58] Field of Search .................... 424/61, 70, 71, 72, 424/47, 62, 78, 358, 365; 132/7; 8/405–407; 514/846, 881

[56] References Cited

U.S. PATENT DOCUMENTS

| | | | |
|---|---|---|---|
| 3,862,906 | 1/1975 | Chambon et al. | 252/95 X |
| 3,956,163 | 5/1976 | Lee | 252/171 |
| 3,959,462 | 5/1976 | Parks et al. | 424/70 |
| 4,009,139 | 2/1977 | Widder et al. | 252/174.24 X |
| 4,158,053 | 6/1979 | Greene et al. | 424/61 |
| 4,240,450 | 12/1980 | Grollier et al. | 424/70 |
| 4,247,538 | 1/1981 | Barker | 424/70 |
| 4,381,294 | 4/1983 | Bouillon et al. | 424/61 |
| 4,445,521 | 5/1984 | Grollier et al. | 424/365 X |

FOREIGN PATENT DOCUMENTS 68419 10/1975 Australia .

OTHER PUBLICATIONS

Feldtman et al, "Adsorption of Polyacrylate Latex on Wool", *Textile Research Journal*, vol. 48, No. 5, pp. 277–280 (May 1978).
Feldtman et al, "Application of Polyacrylates to Wool by an Exhaustion Method", *Textile Research Journal*, vol. 36, No. 10, pp. 935–937 (Oct. 1966).
R. M. Fitch, "Preparation and Characterization of Charge-Stabilized Polymer Colloids", pp. 51–69; Polyelectrolytes and Their Applications; Alan Rembaum et al editors; 1975, D. Reidel Publishing Company, Dordrecht-Holland.
Greenberg and Lester, "Handbook of Cosmetic Materials", 1954, p. 19.
Nowak, "Die Kosmetischen Praparate", p. 394.

*Primary Examiner*—Sidney Marantz
*Assistant Examiner*—Shawn P. Foley
*Attorney, Agent, or Firm*—Fleit, Jacobson, Cohn & Price

[57] ABSTRACT

A composition suitable for treating the hair, nails and/or skin, which comprises, in an appropriate medium, at least one cationic polymer of the polyamine, polyamino polyamide or poly-(quaternary ammonium) type containing amine or ammonium groups in the polymer chain or joined thereto, and at least one anionic latex which is in the form of a colloidal suspension of particles of polymers containing anionic functional groups, in an aqueous or organic liquid phase.

15 Claims, No Drawings

COSMETIC COMPOSITION CONTAINING CATIONIC POLYMERS AND ANIONIC LATEXES

The present invention relates to cosmetic compositions intended for use in the treatment of keratin substances, and in particular hair, nails and skin. The present invention relates more particularly to the use of at least one cationic polymer in combination with at least one anionic latex.

Cationic polymers have already been recommended for use in hair treatment compositions, especially for making the hair easier to comb out and for imparting softness and suppleness thereto. These polymers also make it possible to improve the cosmetic properties of wet and dry hair and to reduce the adverse weighing-down effects of the cationic compounds having a fatty chain which are normally used.

However, these cationic polymers, having substantivity, have the disadvantage of not giving sufficient hold and shine to the hair.

To overcome this disadvantage, we have already proposed to use anionic polymers with cationic polymers. A combination of this kind is described in particular in French Pat. No. 2,383,660. The use of such a combination makes it possible to improve the properties of liveliness, volume, stiffness and hold of the hair.

We have now discovered, according to the present invention, that, by using anionic latices in place of the anionic polymers envisaged in French Pat. No. 2,383,660, it is possible to obtain properties of liveliness, volume, stiffness and hold of the hair which persist for a longer time.

Particularly valuable results have been observed for treatments usually followed by rinsing, such as shampooing, and treatments with lotions or creams followed by rinsing, which are used to obtain a hair-conditioning effect and are applied before or after colouring, bleaching, shampooing, perming or straightening.

The compositions according to the invention can also be used in the form of colouring products, setting lotions, blow-drying lotions, restructuring lotions or bleaching, perming or straightening products.

The present invention therefore provides a composition intended for use in the treatment of the hair, nails or skin, containing at least one cationic polymer and at least one anionic latex in a medium which makes it possible to apply this combination to the hair, nails or skin, as well as a process for treating the hair, nails or skin using a cationic polymer and an anionic latex; it is possible to fix anionic latices to the hair, nails or skin with the aid of a cationic polymer.

The compositions according to the invention are essentially characterised in that they contain, in a suitable medium;

(a) at least one cationic polymer of the polyamine, polyaminoamide or poly-(quaternary ammonium) type containing amine or ammonium groups in the polymer chain or joined thereto; and (b) at least one anionic latex.

The term "anionic latex" as used herein is to be understood as meaning a colloidal suspension of polymer particles in an aqueous or organic liquid phase.

The latices used according to the invention are those containing anionic functional groups which can be introduced by the polymerisation or copolymerisation of anionic monomers by the usual processes, or by combination of the anionic free radical derived from the reaction initiator with the monomer or monomers in question, during the initiation of the polymerisation of the said monomers, or by the juxtaposition of these two processes of synthesis, or alternatively by the introduction of end groups via a chain transfer reaction in the second process using a reaction initiator.

The process using reaction initiators is described in particular in the article by R. M. FITCH entitled "Preparation and Characterization of Charge Stabilized Polymer Colloids" in "Polyelectrolytes and their Applications", 51–69, published by the D. REIDER publishing company.

The latices used more particularly in the compositions according to the invention result from the polymerisation of various monomers, such as styrene, butadiene, acrylonitrile, chloroprene, vinylidene chloride, isoprene, isobutylene, vinyl chloride and the esters of acrylic, methacrylic, vinylacetic, maleic, crotonic and itaconic acids, used by themselves or, where necessary or desired, mixed with one or more of the following ionic monomers: acrylic, methacrylic, itaconic, maleic, crotonic, para-styrenesulphonic, vinylsulphonic, 2-methacryloyloxyethylsulphonic and 2-acrylamido-2-methylpropylsulphonic acids.

The latices can also be obtained by the polymerisation or copolymerisation of the abovementioned ionic monomers.

The latices obtained in accordance with the second process mentioned above result from the use of initiators chosen from Redox systems, peroxides, perphosphates, percarbonates, persulphates, organic peroxyacids such as peracetic acid, and the persulphate/bisulphite/iron mixture.

The functional monomers used in the case of chain transfer reactions may be organic thioacids such as mercaptoacetic acid.

Amongst the anionic latices which can be used according to the invention, there may be mentioned, in particular, the products sold under the following tradenames: KARAMUL 142 ST, which is an acrylic emulsion sold by FRANCONYX; the latices sold under the names PRIMAL B52, PRIMAL K3, PRIMAL TR 485 and PRIMAL AS 95, which consist of aqueous acrylic emulsions sold by ROHM & HAAS and containing between 20 and 50% of solids; APPRETAN ANT, which is an acrylic copolymer dispersion sold by HOECHST; ACRYMUL AM 176 R, which is an aqueous emulsion of an acrylic copolymer containing reactive groups, sold by PROTEX; NATIONAL 125 4477 and 125 4445, which are aqueous dispersions of an acrylic copolymer, and NATIONAL 125, 2833, NATIONAL 125 2869 and NATIONAL 125 2873, which are emulsions of a vinyl acetate/acrylic acid copolymer, sold by NATIONAL ADHESIVES & RESINS; LUCIDENE 347, which is a styrene/acrylic acid emulsion sold by WILLIAMS; SYNTRAN 1026, which is an acrylic acid/ethylene/styrene emulsion sold by INTERPOLYMER CORPORATION; COLAPERLE SPA, which is an aqueous dispersion of an acrylic copolymer, sold by PCUK; and CHEMIGUM LATEX 6271, which is a carboxybutadiene/acrylonitrile copolymer sold by GOODYEAR.

It is self-evident that other anionic latices can be used according to the invention.

The latices used are suitably present in proportions of 0.01 to 10%, and preferably 0.05 to 5%, by weight.

The cationic polymers generally have a molecular weight from 500 to 3,000,000 and preferably from 5,000 to 1,000,000.

These cationic polymers constitute a class well known to cosmetology specialists, and are described especially in French Patents and French Patent Applications Nos. 2,077,143, 1,492,597, 2,162,025, 2,280,361, 2,252,840, 2,368,508, 1,583,363, 2,080,759, 2,190,406, 2,320,330, 2,270,846, 2,316,271, 2,336,434, 2,189,434, 2,413,907, 2,393,573 and 2,434,821, and also in U.S. Pat. Nos. 3,589,978, 4,031,307, 3,227,615, 2,961,347, 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, 4,027,020, 4,131,576 and 4,185,087, and in European Patent Applications Nos. 17,121 and 17,122.

The cationic polymers used according to the invention are especially polymers of the polyamine, polyaminoamide or poly-(quaternary ammonium) type, the amino and/or ammonium group forming part of the polymer chain or being joined thereto. Amongst these polymers, the following may be mentioned in particular:

(1) Vinylpyrrolidone/dialkylaminoalkyl acrylate or methacrylate copolymers (quaternised or unquaternised), such as those sold under the name Gafquat by the Gaf Corp., such as "copolymer 845" and Gafquat 734 or 755, described in greater detail in particular in French Pat. No. 2,077,143 and French Patent Application No. 2,393,573.

(2) Cellulose ether derivatives containing quaternary ammonium groups, such as those described in French Pat. No. 1,492,597, and especially the polymers sold under the name JR, such as JR 125, JR 400 and JR 30M, and under the name LR, such as LR 400 and LR 30M, by the Union Carbide Corp., and cationic cellulose derivatives, such as the products sold under the names CELQUAT L 200 and CELQUAT H100 by National Starch and described in U.S. Pat. No. 4,131,576.

(3) Cationic polysaccharides, such as those described in U.S. Pat. Nos. 3,589,978 and 4,031,357, and in particular Jaguar C. 13 S sold by Meyhall.

(4) Cationic polymers chosen from the group comprising:

(a) Polymers containing units of the formula:

$$-A-Z-A-Z-\quad\text{(I)},$$

in which A denotes a radical containing two amino groups, preferably a piperazinyl radical, and Z denotes the symbol B or B'; B and B', which are identical or different, denote a divalent radical which is a straight-chain or branched-chain alkylene radical which contains up to 7 consecutive carbon atoms in the main chain, which is unsubstituted or substituted by hydroxyl groups and which can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amine, alkylamine, alkenylamine, benzylamine, amine oxide, quaternary ammonium, amide, imide, alcohol, ester and/or urethane groups; these polymers and the process for their preparation are described in French Pat. No. 2,162,025.

(b) Polymers containing units of the formula:

$$-A-Z_1-A-Z_1-\quad\text{(II)},$$

in which A denotes a radical containing two amino groups, preferably a piperazinyl radical, and $Z_1$ denotes the symbol $B_1$ or $B'_1$ and denotes the symbol $B'_1$ at least once; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more nitrogen atoms, the nitrogen atom being substituted by an alkyl chain which has from 1 to 4 carbon atoms, and preferably 4 carbon atoms, which is optionally interrupted by an oxygen atom and which optionally contains one or more hydroxyl groups.

The polymers of the formula (II) and the process for their preparation are described in French Pat. No. 2,280,361.

(c) The alkylation products of the polymers of the formulae (I) and (II) indicated above under (a) and (b) with alkyl and benzyl halides and lower alkyl tosylates or mesylates, and the oxidation products of the said polymers.

(5) Optionally alkylated, crosslinked polyaminopolyamides chosen from the group comprising at least one water-soluble crosslinked polymer obtained by crosslinking a polyaminopolyamide (A) prepared by the polycondensation of an acid compound with a polyamine. The acid compound is chosen from (i) organic dicarboxylic acids, (ii) aliphatic monocarboxylic and dicarboxylic acids with a double bond, (iii) esters of the above-mentioned acids, preferably the esters with lower alkanols having from 1 to 6 carbon atoms, and (iv) mixtures of these compounds. The polyamine is chosen from amongst bis-primary, mono-secondary or bis-secondary polyalkylenepolyamines. Up to 40 mol % of this polyamine can be replaced by a bis-primary amine, preferably ethylenediamine, or by a bis-secondary amine, preferably piperazine, and up to 20 mol % can be replaced by hexamethylenediamine. The crosslinking is carried out by means of a crosslinking agent (B) chosen from amongst epihalogenohydrins, diepoxides, dianhydrides, unsaturated anhydrides and bis-unsaturated derivatives, suitably in proportions of 0.025 to 0.35 mol of crosslinking agent per amino group of the polyaminopolyamide (A). These polymers and their preparation are described in greater detail in French Pat. No. 2,252,840.

The alkylation can be carried out, if appropriate, with glycidol, ethylene oxide, propylene oxide or acrylamide.

The polyaminopolyamides (A) themselves can also be used according to the invention.

(6) The crosslinked polyaminopolyamides obtained by crosslinking a polyaminopolyamide (A) described above by means of a crosslinking agent chosen from the group comprising:

(I) compounds chosen from the group comprising (1) bis-halogenohydrins, (2) bis-azetidinium compounds, (3) bis-halogenoacyl-diamines and (4) bis-(alkyl halides);

(II) the oligomers obtained by reacting a compound (a) chosen from the group comprising (1) bis-halogenohydrins, (2) bis-azetidinium compounds, (3) bis-halogenoacyl-diamines, (4) bis-(alkyl halides), (5) epihalogenohydrins, (6) diepoxides and (7) bis-unsaturated derivatives, with a compound (b) which is a difunctional compound reactive towards the compound (a); and (III) the quaternisation product of a compound chosen from the group comprising the compounds (a) and the oligomers (II) and containing one or more tertiary amine groups which can be totally or partially alkylated, with an alkylating agent (c) preferably chosen from the group comprising methyl or ethyl chlorides, bromides, iodides, sulphates, mesylates and tosylates, benzyl chloride or bromide, ethylene oxide, propylene oxide and glycidol, the crosslinking being carried out by means of, say, 0.025 to 0.35 mol, in particular by means of 0.025 to 0.2 mol and more particularly by means of 0.025 to 0.1 mol, of crosslinking agent per amine group of the polyaminopolyamide.

These crosslinking agents and these polymers, and also the process for their preparation, are described in French Pat. No. 2,368,508.

(7) The polyaminopolyamide derivatives resulting from the condensation of a polyalkylenepolyamine with a polycarboxylic acid, followed by alkylation by means of difunctional agents, such as adipic acid/dialkylaminohydroxyalkyl-dialkylenetriamine copolymers in which the alkyl radical contains 1 to 4 carbon atoms and preferably denotes methyl, ethyl or propyl, which are described in French Pat. No. 1,583,363.

Amongst these compounds, there may be mentioned especially the adipic acid/dimethylaminohydroxypropyldiethylenetriamine copolymers sold under the names Cartarétine F, F4 or F8 by SANDOZ.

(8) The polymers obtained by reacting a polyalkylenepolyamine containing two primary amine groups and at least one secondary amine group with a dicarboxylic acid chosen from amongst diglycolic acid and saturated aliphatic dicarboxylic acids having 3 to 8 carbon atoms, the molar ratio of the polyalkylenepolyamine to the dicarboxylic acid being from 0.8:1 to 1.4:1, and the resulting polyaminoamide being reacted with epichlorohydrin in a molar ratio of epichlorohydrin to the secondary amine groups of the polyaminoamide of 0.5:1 to 1.8:1; these polymers are mentioned in U.S. Pat. Nos. 3,227,615 and 2,961,347.

The polymers of this type include that sold under the name HERCOSETT 57 by Hercules Incorporated and that sold under the name PD 170 or DELSETTE 101 by Hercules in the case of the adipic acid/epoxypropyldiethylenetriamine copolymer.

(9) Cyclic polymers generally having a molecular weight of 20,000 to 3,000,000, such as homopolymers containing, as the main constituent of the chain, units corresponding to the formula (III) or (III'):

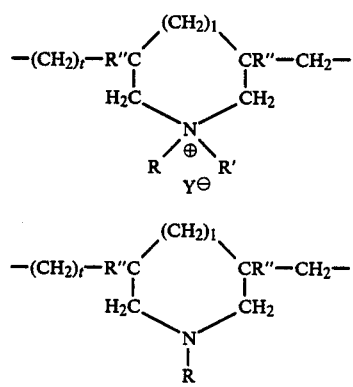

in which 1 and t are equal to 0 or 1 with 1+t=1, R" denotes hydrogen or methyl, R and R' independently of one another denote an alkyl group having from 1 to 22 carbon atoms, a hydroxyalkyl group in which the alkyl group preferably has 1 to 5 carbon atoms, or a lower amidoalkyl group, and R and R' can denote, together with the nitrogen atom to which they are attached, heterocyclic groups such a piperidinyl or morpholinyl; $Y^\ominus$ is an anion such as bromide, chloride, acetate, borate, citrate, tartrate, bisulphate, bisulphite, sulphate or phosphate and also copolymers containing units of the formula III or III' and units derived from acrylamide or from diacetone-acrylamide.

Amongst the quaternary ammonium polymers of the type defined above, there may be mentioned the dimethyldiallylammonium chloride homopolymer sold under the name MERQUAT 100 and having a molecular weight of less than 100,000, and the dimethyldiallylammonium chloride/acrylamide copolymer having a molecular weight of more than 500,000 and sold under the name MERQUAT 550 by MERCK.

These polymers are described in French Pat. No. 2,080,759 and its Certificate of Addition No 2,190,406.

(10) Poly-(quaternary ammonium) compounds of the formula:

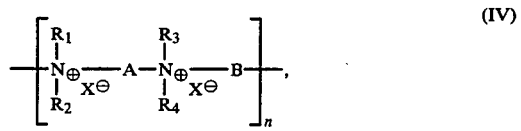

in which $R_1$ and $R_2$, and $R_3$ and $R_4$, which are identical or different, represent aliphatic, alicyclic or arylaliphatic radicals containing at most 20 carbon atoms, or lower hydroxyaliphatic radicals, or alternatively $R_1$ and $R_2$, and $R_3$ and $R_4$, together or separately form, with the nitrogen atoms to which they are attached, heterocyclic rings optionally containing a second hetero-atom other than nitrogen, or alternatively $R_1$, $R_2$, $R_3$ and $R_4$ represent a group

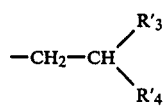

$R'_3$ denoting hydrogen or lower alkyl and $R'_4$ denoting

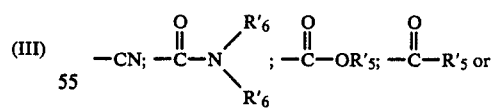

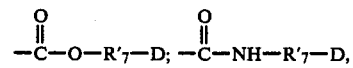

$R'_5$ denoting lower alkyl, $R'_6$ denoting hydrogen or lower alkyl, $R'_7$ denoting alkylene and D denoting a quaternary ammonium group; A and B can represent polymethylene groups containing from 2 to 20 carbon atoms, which can be linear or branched and saturated or unsaturated and which can contain, inserted into the main chain, one or more aromatic rings such as the group

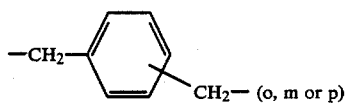

or one or more groups $-(CH_2)_n-Y-(CH_2)_n-$, Y denoting O, S, SO, SO$_2$,

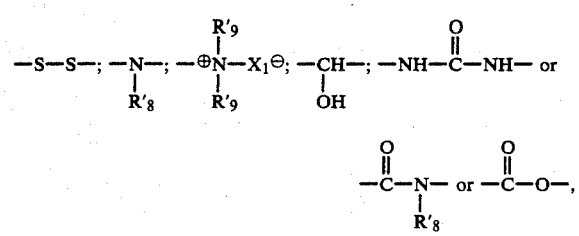

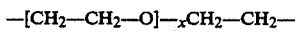

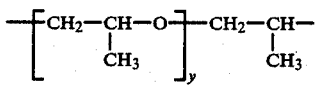

with $X_1^\ominus$ denoting an anion derived from a mineral or organic acid, n denoting 2 or 3, $R'_8$ denoting hydrogen or lower alkyl and $R'_9$ denoting lower alkyl, or alternatively A and $R_1$ and $R_3$ form a piperazine ring with the two nitrogen atoms to which they are attached; moreover, if A denotes a linear or branched, saturated or unsaturated alkylene or hydroxyalkylene radical, B can also denote a group: $-(CH_2)_n-CO-D-OC-(CH_2)_n-$, in which D denotes:

(a) a glycol radical of the formula $-O-Z-O-$, in which z denotes a linear or branched hydrocarbon radical or a group corresponding to the formulae:

$$-[CH_2-CH_2-O]-_xCH_2-CH_2-$$

or $$-\left[CH_2-CH-O\atop\hspace{1em}CH_3\right]_y-CH_2-CH-\atop\hspace{4em}CH_3$$

in which x and y denote an integer from 1 to 4, representing a definite and unique degree of polymerisation (in the case of a single compound), or any number from 1 to 4, representing an average degree of polymerisation (in the case of a mixture);

(b) a bis-secondary diamine radical, such as a piperazine derivative;

(c) a bis-primary diamine radical of the formula: $-NH-Y-NH-$, in which Y denotes a linear or branched hydrocarbon radical or the divalent radical $-CH_2-CH_2-S-S-CH_2-CH_2-$; or (d) a ureylene group of the formula $-NH-CO-NH-$; n is such that the molecular weight is generally from 1,000 to 100,000 and $X^\ominus$ denotes an anion.

Polymers of this type are described in particular in French Pat. Nos. 2,320,330 and 2,270,846, French Applications Nos. 2,316,271, 2,336,434 and 2,413,907, and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid and containing at least one unit:

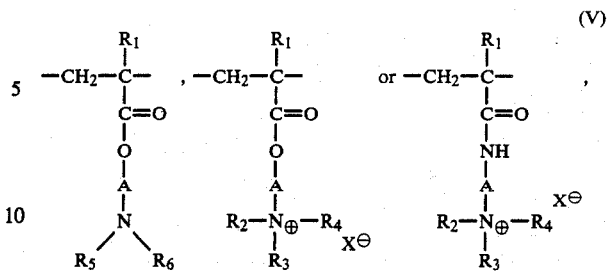

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$, which are identical or different, denote an alkyl group having 1 to 18 carbon atoms or a benzyl group, $R_5$ and $R_6$ denote H or alkyl having 1 to 6 carbon atoms, and X denotes methosulphate or halogen, such as chlorine or bromine.

The comonomer or comonomers which can be used include: acrylamide, methacrylamide, diacetoneacrylamide, acrylamide and methacrylamide substituted on the nitrogen by one or more lower alkyls, acrylic and methacrylic acid esters, vinylpyrrolidone and vinyl esters.

The following may be mentioned by way of example:
the products listed under the names Quaternium 38, 37, 49 and 42 in the Cosmetic Ingredient Dictionary,
the acrylamide/beta-methacryloyloxyethyl-trimethylammonium methosulphate copolymers sold under the names Reten 205, 210, 220 and 240 by Hercules,
the aminoethylacrylate phosphate/acrylate copolymer sold under the name Catrex by National Starch, and
the graft crosslinked cationic copolymers, having a molecular weight of 10,000 to 1,000,000 and preferably of 15,000 to 500,000, which results from the copolymerisation of:
(a) at least one cosmetic monomer,
(b) dimethylaminoethyl methacrylate,
(c) polyethylene glycol and
(d) a polyunsaturated crosslinking agent,
these copolymers being described in French Pat. No. 2,189,434.

The cosmetic monomer can be of a very wide variety of types, for example a vinyl ester, an allyl or methallyl ester, an acrylate or methacrylate of a saturated alcohol having from 1 to 18 carbon atoms, an alkyl vinyl ether, an olefine, a vinylic heterocyclic derivative, a dialkyl or N,N-dialkylaminoalkyl maleate or an unsaturated acid anhydride.

(12) Quaternary polymers of vinylpyrrolidone and vinylimidazole, such as LUVIQUAT FC 905 sold by BASF.

(13) Cationic silicone polymers, such as those described in European Applications Nos. 17,121 and 17,122, U.S. Pat. No. 4,185,087, Japanese Patent Application No. 80/66,506 and Austrian Patent Application No. 71/01,171, or those listed in the CTFA Dictionary under the same AMODIMETHICONE, such as the product marketed in a mixture with other ingredients under the name "DOW CORNING 929 cationic emulsion".

(14) Cationic derivatives of starches or of starch ethers, such as those described in French Patent Application No. 2,434,821, especially the polymer sold under the name LAB 358 by ROQUETTE.

Other cationic polymers which can be used include polyalkyleneimines, in particular polyethyleneimines, polymers containing vinylpyridine units or vinylpyridinium units in the chain, polyamine/epichlorohydrin condensates, poly-(quaternary ureylene) compounds and chitin derivatives.

The cationic polymers used according to the invention are preferably present in proportions of 0.01 to 10% and in particular from 0.05 to 5% by weight.

In a preferred embodiment, the compositions can contain, in addition to the cationic polymers and the anionic latices, surface-active which can be anionic, non-ionic, cationic and amphoteric surface-active agents or mixtures thereof.

The concentration of surface-active agent can be up to 70% by weight of active ingredient and is preferably from 0.5 to 50% by weight. The surface-active agents can be used by themselves or in a mixture.

Amongst the anionic surface-active agents, which can be used by themselves or in a mixture, there may be mentioned, in particular, the alkali metal salts, the ammonium salts, the amine salts or the aminoalcohol salts of the following compounds:

alkyl-sulphates, alkyl-ether-sulphates, alkylamide-sulphates and alkylamide-ether-sulphates, alkylaryl-polyether-sulphates and monoglyceride-sulphates, alkylsulphonates, alkylamidesulphonates, alkylarylsulphonates, α-olefinesulphonates and paraffinsulphonates, alkyl-sulphosuccinates, alkyl-ether-sulphosuccinates and alkylamide-sulphosuccinates, alkyl-sulphosuccinamates, alkyl-sulphoacetates and alkyl-polyglycerolcarboxylates, alkyl-phosphates and alkyl-ether-phosphates, and alkylsarcosinates, alkylpolypeptidates, alkylamidopolypeptidates, alkylisethionates and alkyltaurates.

The alkyl radical in all these compounds generally denotes a linear chain having 12 to 18 carbon atoms.

Other anionic surface-active agents include fatty acids such as oleic acid, ricinoleic acid, palmitic acid, stearic acid and acids derived from copra oil or from hydrogenated copra oil.

The following may also be mentioned:

acyllactylates in which the alkyl radical contains from 8 to 20 carbon atoms, and carboxylic acids of polyglycol ethers, corresponding to the formula:

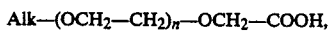

Alk—(OCH$_2$—CH$_2$)$_n$—OCH$_2$—COOH, in the form of bases or salts, in which the substituent Alk corresponds to a linear chain having from 12 to 18 carbon atoms and in which n is an integer from 5 to 15.

Amongst the non-ionic surface-active agents, which can be used by themselves or in a mixture, the following may be mentioned in particular: polyoxyethyleneated, polyoxypropyleneated or polyglycerolated alcohols, alkylphenols and fatty acids with a linear fatty chain containing 8 to 18 carbon atoms and most frequently containing 2 to 30 mols of ethylene oxide. There may also be mentioned ethylene oxide/propylene oxide copolymers, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

Other compounds belonging to this class are: the condensation products of a monoalcohol, an α-diol, an alkylphenol, an amide or a diglycolamide with glycidol, such as the compounds corresponding to the formula:

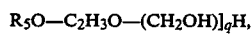

R$_4$—CHOH—CH$_2$—O—(CH$_2$—CHOH—CH$_2$—O)$_{\overline{p}}$H, in which R$_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p is from 1 to 10, such as the compounds described in French Pat. No. 2,091,516;

compounds corresponding to the formula:

R$_5$O—C$_2$H$_3$O—(CH$_2$OH)]$_q$H, in which R$_5$ denotes an alkyl, alkenyl or alkylaryl radical and q has a statistical value of 1 to 10, such as the compounds described in French Pat. No. 1,477,048; and compounds corresponding to the formula:

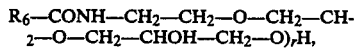

R$_6$—CONH—CH$_2$—CH$_2$—O—CH$_2$—CH$_2$—O—CH$_2$—CHOH—CH$_2$—O)$_r$H, in which R$_6$ denotes a linear or branched, saturated or unsaturated aliphatic radical, or a mixture of such radicals, which can optionally contain one or more hydroxyl groups, has from 8 to 30 carbon atoms and is of natural or synthetic origin, and r represents an integral or decimal number from 1 to 5 and denotes the average degree of condensation (in the case of a reaction mixture), such as the compounds described in French Pat. No. 2,328,763.

Amongst the cationic surface-active agents, which can be used by themselves or in a mixture, the following may be mentioned in particular: fatty amine salts such as alkylamine acetates, quaternary ammonium salts such as alkyldimethylbenzylammonium, alkyltrimethylammonium, dialkyldimethylammonium and alkyldimethylhydroxyethylammonium chlorides and bromides, alkylamidoethyltrimethylammonium methosulphates, in which the alkyl radicals preferably have 1 to 22 carbon atoms, quaternary halides of gluconamide, such as those described in U.S. Pat. No. 3,766,267, quaternary halides of mink oil amide, such as those described in U.S. Pat. No. 4,012,398, quaternary derivatives of a dialkylaminopropylamide fatty halogenoalkanoate, such as those described in U.S. Pat. No. 4,038,294, quaternary ammonium derivatives of lanolin fatty acids, such as those described in U.S. Pat. No. 4,069,347, alkylpyridinium salts and imidazoline derivatives.

There may also be mentioned compounds of cationic character, such as amine oxides e.g. alkyldimethylamine oxides or alkylaminoethyldimethylamine oxides.

Amongst the amphoteric surface-active agents which can be used, there may be mentioned, more particularly, alkylamino-monopropionates and alkylamino-dipropionates, betaines such as N-alkylbetaines, N-alkylsulphobetaines and N-alkylamidobetaines, cycloimidinium compounds such as alkylimidazolines, and asparagine derivatives.

The compositions according to the invention can also contain other adjuvants normally used in cosmetics, and, more particularly, cosmetically acceptable solvents which can be used in place of or in combination with water. There may be mentioned, more particularly, mono alcohols such as alkanols having 1 to 8 carbon atoms, polyols, glycol ethers and their esters, and fatty acid esters of lower alcohols, which can be used singly or in a mixture, at concentrations up to 95% by weight.

The compositions can also contain electrolytes such as alkali metal or alkaline earth metal salts, and especially the halides, such as the chloride or bromide, the sulphates, the carbonates or the salts of organic acids, in particular, the acetates or lactates of sodium, potassium or lithium, or alternatively the carbonates, silicates, nitrates, acetates, gluconates, panthothenates and lactates of calcium, magnesium or strontium.

When used according to the invention, the salts can be used singly or in a mixture and can be present in proportions up to, say, 10% by weight of active ingredient and preferably from 0.5 to 5% by weight.

The compositions according to the present invention can be used as such for treating the hair, nails or skin, or can be used as "bases or carriers" forming part of cosmetic formulations which also contain an appropriate proportion of active product and which are intended for application to the skin or hair in order to protect it against attack by atmospheric agents or actinic rays, and to promote the action of any other active product intended for the skin, hair or nails.

In addition to the cationic polymer or polymers or the anionic latex or latices, the compositions can contain adjuvants normally used in cosmetics, such as perfumes, dyestuffs which can serve to colour the composition itself or the hair, skin or nails, preservatives, sequestering agents, thickeners, emulsifying agents, softeners, and foam stabilisers, depending on the application envisaged.

The compositions according to the invention can be presented in a variety of forms, such as liquids, creams, emulsions and gels.

These compositions can also be packaged in aerosol cans, in which case they can be applied either in the form of an aerosol spray or in the form of an aerosol foam.

If the cosmetic compositions of this invention are used to treat the hair, in particular lively hair, they can be presented more particularly in the form of colouring or bleaching products, shampoos, rinse-off lotions or creams to be applied before or after shampooing, before or after colouring or bleaching or before or after perming or straightening, setting lotions, blow-drying lotions, restructuring lotions, perming lotions or straightening lotions.

When the compositions constitute shampoos, the concentration of surface-active agent is generally from 3 to 50% by weight and preferably from 3 to 20%, and the pH is generally from 3 to 10.

The composition may also form rinse-off lotions or creams to be applied mainly before or after shampooing. These lotions can be aqueous or aqueous-alcoholic dispersions, emulsions, thickened lotions or gels.

If the compositions are presented in the form of emulsions, they can be non-ionic or anionic. The non-ionic emulsions generally consist mainly of a mixture of oil and/or fatty alcohol with a polyoxyethyleneated alcohol such as polyoxyethyleneated stearyl or cetylstearyl alcohol.

The anionic emulsions are generally based on soaps.

If the compositions are presented in the form of thickened lotions or gels, they contain thickeners, in the presence or absence of solvents. Thickeners which can be used include sodium alginate, gum arabic or cellulose derivatives such as methylcellulose, hydroxymethylcellulose, hydroxyethylcellulose, hydroxypropylcellulose or hydroxypropylmethylcellulose. The lotions can also be thickened using a mixture of polyethylene glycol and polyethylene glycol stearate or distearate or a mixture of phosphoric acid ester and amide. The concentration of thickener is generally 0.5 to 30% by weight and preferably from 0.5 to 15% by weight. The pH of the rinse-off lotions is generally from 3 to 9.

If the compositions according to the invention are presented in the form of styling lotions, shaping lotions or so-called setting lotions, these lotions generally contain, in aqueous, alcoholic or aqueous-alcoholic solution, the components of the combination defined above, optionally together with anti-foam agents.

If the compositions of the present invention constitute dyeing compositions for keratin fibres, they contain, in addition to the cationic polymer (or polymers) and the anionic latex (or latices), at least one oxidation dyestuff precursor and/or one direct dyestuff and, if appropriate, various adjuvants enabling the compositions to be presented in the form of creams, gels or lotions described above.

The compositions can also contain antioxidants, sequestering agents or any other adjuvant normally used in this type of composition.

The pH of these dyeing compositions is generally from 7 to 11 and can be adjusted to the desired value by adding an alkalizing agent such as aqueous ammonia solution, alkali metal hydroxides, alkali metal or ammonium carbonates, alkylamines, alkanolamines or mixtures thereof.

Also, the combination according to the invention can be used in compositions intended for waving or straightening the hair. This composition contains, in addition to the cationic polymer (or polymers) and the anionic latex (or latices), one or more reducing agents and optionally other adjuvants normally used in this type of composition, and is used together with a neutralising (or oxidising) composition.

Suitable reducing agents include sulphites and mercaptans and more particularly thioglycolates or thiolactates or mixtures thereof.

The neutralising composition contains an oxidising agent such as hydrogen peroxide or alkali metal bromates or perborates.

These compositions can also be packaged in aerosol cans.

If the compositions according to the present invention are dispensed in the form of an aerosol spray or foam, the propellant gases used to pressurise the cosmetic formulations are typically present in an amount not exceeding 25% and preferably not exceeding 15%, based on the total weight of the composition. Propellant gases which can be used include carbon dioxide, nitrogen, nitrous oxide, volatile hydrocarbons such as butane, isobutane, propane and mixtures thereof, and non-hydrolysable chlorohydrocarbons and/or fluorohydrocarbons such as those sold under the name FREON by Du Pont de Nemours, in particular the fluorochlorohydrocarbons, such as dichlorodifluoromethane, or Freon 12, and dichlorotetrafluoroethane, or Freon 114. These propellants can be used singly or in combination; a mixture of Freon 114 and Freon 112 in proportions from from 40:60 to 60:20 may be mentioned in particular.

Another embodiment of the process according to the invention consists in forming the combination of the cationic polymer with the anionic latex in situ, for example on the fibres, and in particular on the hair, by applying, in a first step, a composition presented, for example, in the form of a pre-lotion and containing the cationic polymer, and, in a second step, a composition such as a shampoo, containing the anionic latex such as defined above.

According to another modified embodiment of the invention, a shampoo containing the cationic polymer can be applied in a first step and a composition, such as a lotion, containing the anionic latex can be applied in a second step.

Another possible procedure is to use a perming composition (1° reducing step), straightening composition, colouring composition or bleaching composition containing the cationic polymer, and to follow this treatment by a treatment with a composition containing the anionic latex, the latter being placed in a composition which can be an oxidising solution, a shampoo or a simple lotion.

Another possible procedure is successively to use a first shampoo containing the cationic polymer and, in a second step, a second shampoo containing the anionic latex, it being possible for the pH of the compositions applied in these two steps to be different and to be adjusted so that the conditions at the time of application of the composition containing the anionic latex permit a good deposition of the combination according to the invention on the fibres to be treated.

If the compositions are used for application to the skin, they can be presented in the form of an aftershave lotion, toilet water or shaving foam, for example.

The following Examples further illustrate the present invention.

EXAMPLE 1

The following rinse-off composition is prepared:

| | |
|---|---|
| Quaternary polyvinylpyrrolidone copolymer having a molecular weight of 1,000,000, marketed under the name Gafquat 755 by General Anilin | 0.5 g of active ingredient |
| Arylic copolymer dispersion sold under the name APPRETAN ANT by Hoechst | 4 g of active ingredient |
| 50/50 mixture of cetyl alcohol and stearyl alcohol | 3 g |
| Hydroxyethylcellulose sold under the name CELLOSIZE QP 4400 H by Union Carbide | 0.8 g |
| Dimethyldistearylammonium chloride | 0.3 g |
| Perfume - preservative - dyestuff q.s. | |
| Water q.s.p. | 100 g |
| pH = 7 (hydrochloric acid) | |

This composition is applied to clean hear. After an interval of 3 minutes, the hair is rinsed.

It is found that the wet hair is easy to comb out and soft. After drying, the hair is shiny, smooth, lively and stiff and is easy to style.

EXAMPLE 2

The following rinse-off composition is prepared:

| | |
|---|---|
| Polymer resulting from the polycondensation of equimolar amounts of adipic acid and diethylenetriamine, followed by cross-linking with epichlorohydrin (11 mols of epichlorohydrin per 100 amine groups) | 0.7 g of active ingredient |
| Aqueous acrylic emulsion sold under the name PRIMAL K3 by Rohm and Haas | 5 g of active ingredient |
| Mixture of cetyl-stearyl alcohol and cetyl-stearyl alcohol oxyethyleneated with 15 mols of ethylene oxide | 3 g |
| Hydroxyethylcelluose sold under the name CELLOSIZE QP 4400 H by Union Carbide | 0.6 g |
| Mixture of fatty alcohols and oxyethyleneated products, sold under the name POLAWAX GP 200 by Croda | 1.5 g |
| Perfume - preservative - dyestuff q.s. | |
| Water q.s.p. | 100 g |
| pH = 7.3 (sodium hydroxide) | |

This composition is applied in the same way as that of Example 1.

After rinsing, it is found that the wet hair is easy to comb out. After drying, the hair acquires noteworthy stiffness and hold.

EXAMPLE 3

The following shampoo is prepared:

| | |
|---|---|
| Polymer of the formula: 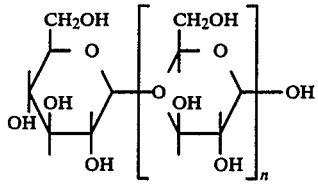 which can be prepared as described in French Patent Application 2,270,846 | 1.2 g of active ingredient |
| Aqueous dispersion of an acrylic copolymer, sold under the name NATIONAL 125 4477 by National Adhesives and Resins | 3 g of active ingredient |
| Glucoside alkyl ether of the general formula: | 36 g |

$$\begin{bmatrix} \text{CH}_2\text{OH} \\ \text{O} \\ \text{OH} \\ \text{OH} \end{bmatrix} \begin{bmatrix} \text{CH}_2\text{OH} \\ \text{O} \\ \text{OH} \\ \text{OH} \end{bmatrix}_n \text{OH}$$

n = 0, 1, 2 and so on
R = Linear $C_8H_{10}$-alkyl
sold as a product containing 30% of active ingredient under the name TRITON CG 110 by Rohm and Haas

| | |
|---|---|
| Non-ionic surface-active agent based on polyglycerolated lauryl alcohol (4.2 mols of glycerol) as a solution containing 60% of active ingredient of the statistical formula | 12 g |

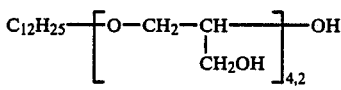

| | |
|---|---|
| Perfume - preservative - dyestuff q.s. | |
| Water q.s.p. | 100 g |
| pH = 8 with sodium hydroxide | |

20 ml of this composition are applied in two stages to wet dirty hair. The composition rapidly develops a copious soft foam which penetrates the hair and is easy to rinse off. The wet hair is easy to comb out. After drying, it is smooth, shiny, stiff and lively. The hair possesses a noteworthy cohesion and a good hold.

EXAMPLE 4

The following washing composition is prepared:

| | |
|---|---|
| Quaternised cellulose sold under the name JR. 400 by Union Carbide | 1 g of active ingredient |
| Aqueous dispersion of an acrylic copolymer, sold under the name NATIONAL 125 4445 by National Adhesives and Resins | 4.5 g of active ingredient |
| Alkyl($C_{12}C_{18}$)—dimethylcarboxymethyl-ammonium hydroxide sold under the name DEHYTON AB by 30 Henkel, containing 30% of active ingredient | 36 g |
| Triethanolamine salt of lauroylkeratinic acid, containing 24% of active ingredient, sold under the name LIPOPROTEOL LK by Rhone-Poulenc | 20 g |
| Dyestuffs - preservatives - perfumes q.s. Water q.s.p. pH = 8.2 with sodium hydroxide | 100 g |

This composition, applied in the same way as that of Example 3, produces a copious foam which is easy to rinse off. The wet hair is very soft and, after drying, the hair has bulk and stiffness.

EXAMPLE 5

The following washing composition is prepared:

| | |
|---|---|
| Epichlorohydrin/piperazine polycondensate having a molecular weight of 1,500 to 2,000 | 1 g of active ingredient |
| Aqueous acrylic emulsion sold under the name PRIMAL TR 485 by Rohm and Haas | 2.5 g of active ingredient |
| Sodium chloride | 4 g |
| Sodium salt of sulphated alkanol($C_{12}$–$C_{14}$) oxyethyleneated with 2.2 mols of ethylene oxide, containing 25% of active ingredient | 32 g |
| Triethanolamine salt of the condensation product of copra acid and animal protein hydrolysate, containing 40% of active ingredient and sold under the name MAYPON 4 CT by STEPAN | 25 g |
| Dyestuffs - preservatives - perfume q.s. Water q.s.p. pH 7.8 | 100 g |

This composition, applied in the same way as that of Example 3, makes the wet hair easy to comb out and gives the dried hair a good degree of liveliness and stiffness.

EXAMPLE 6

A leave-on shaping lotion is prepared

| | |
|---|---|
| Mixture of amodimethicone, "tallowtrimonium chloride" and nonoxynol - 10 according to the CTFA (Cosmetic Ingredient Dictionary, 1982 Edition), sold under the name Dow Corning 929 cationic emulsion by DOW CORNING | 0.8 g of active ingredient |
| Emulsion of vinyl acetate/maleic anhydride copolymer, sold under the name RHODOPAS AM 0 12 by RHONE-POULENC Perfume, preservative, dyestuff Water q.s.p. | 2 g of active ingredient<br>100 g |

The hair to which this composition has been applied has a good hold.

EXAMPLE 7

An after-shave emulsion is prepared

| | |
|---|---|
| Dimethyldiallylammonium chloride/acrylamide copolymer having a molecular weight >500,000, sold under the name MERQUAT 550 by MERCK | 0.6 g of active ingredient |
| Emulsion of vinyl acetate homopolymer, sold under the name RHODOPAS A 0 12 P by RHONE-POULENC Perfume, dyestuff, preservative | 1 g of active ingredient |
| Water q.s.p. | 100 g |

The skin has a soft feel after application.

EXAMPLE 8

The following two-step treatment is carried out 1. 1st step:

A shampoo containing the following cationic polymer is applied:

| | |
|---|---|
| Adipic acid/dimethylaminohydroxypropyl-diethylenetriamine copolymer sold under the name CARTARETINE F4 by SANDOZ | 1 g of active ingredient |
| Glycoside alkyl ether sold at a concentration of 30% of active ingredient under the name TRITON CG 110 by SEPPIC | 12 g of active ingredient |
| Hydroxyethylcellulose sold under the name NATROSOL 250 HHR by HERCULES | 1 g of active ingredient |
| Water q.s.p. | 100 g |

2. 2nd step:

A lotion containing the following anionic latex is applied:

| | |
|---|---|
| Carboxybutadiene/acroylonitrile copolymer sold under the name CHEMIGUM LATEX 6271 sold by GOODYEAR | 0.3 g of active ingredient |
| Hydroxyethylcellulose sold under the name NATROSOL 250 HHR by HERCULES Preservative, perfume | 0.5 g of active ingredient |
| Water q.s.p. | 100 g |

The hair treated by a two-step process using the above compositions is soft to the touch and has a good hold.

EXAMPLE 9

A hair-conditioning foam is prepared

| | |
|---|---|
| Cationic quaternary polymer having a composition of 5% of vinylpyrrolidone and 95% of vinylimidazole, sold under the name LUVIQUAT FC 905 by BASF | 1 g of active ingredient |
| Emulsion of carboxybutadiene/acrylonitrile copolymer, sold under the name CHEMIGUM LATEX 6271 by GOODYEAR | 0.5 g of active ingredient |
| Lauryl alcohol polyoxyethyleneated with 12 mols of ethylene oxide | 2 g of active ingredient |
| Perfume, preservative Water q.s.p. | 100 g |

This composition is introduced into an aerosol device at a rate of 90 g to 10 g of Freon F 12.

The foam is applied to clean wet hair.

After an interval of one minute, the hair is rinsed.

It is found that the wet hair is easy to comb out and soft.

After setting and drying, the hair is shiny, smoother and more supple.

The hair is easy to style.

EXAMPLE 10

A shaving foam is prepared

| | |
|---|---|
| Stearic acid | 6.3 g of active ingredient |
| Copra fatty acid | 2.7 g of active ingredient |
| Sorbitol | 7 g of active ingredient |
| Dimethyldiallylammonium chloride/acrylamide copolymer of molecular weight >500,000, sold under the name MERQUAT 550 by MERCK | 0.2 g of active ingredient |
| Emulsion of vinyl acetate homopolymer, sold under the name RHODOPAS A 0 12 P by RHONE-POULENC | 0.35 g of active ingredient |
| Triethanolamine | 4.6 g of active ingredient |
| Preservative, perfume | |
| Water q.s.p. | 100 g |

This composition is introduced into an aerosol device at a rate of 90 g to 10 g of Freon F 12.

We claim:

1. A process for treating hair, nails and/or skin, which comprises applying to hair, nails and/or skin a cosmetically acceptable medium containing about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, and about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii).

2. A process according to claim 1 in which the latex results from the polymerisation of one or more monomers which are styrene, butadiene, acrylonitrile, chloroprene, vinylidene chloride, isoprene, isobutylene, vinyl chloride or the esters of acrylic, methacrylic, maleic, vinylacetic, crotonic and itaconic acids, alone or with one or more ionic monomers which are acrylic, methacrylic, itaconic, maleic, crotonic, para-styrenesulphonic, vinylsulphonic, 2-methacryloyloxyethylsulphonic or 2-acryl-amido-2-methylpropylsulphonic acids.

3. A process according to claim 2, in which the latex is an emulsion of an acrylic or methacrylic polymer or copolymer.

4. A process according to claim 1 in which the cationic polymer is (1) a quaternised or unquaternised vinylpyrrolidone/-dialkylaminoalkyl acrylate or methacrylate copolymer, (2) a cellulose ether derivative containing quaternary ammonium groups, or a quaternary cellulose derivative, (3) a cationic polysaccharide, (4) a cationic polymer containing units of the formula —A—Z—A—Z—(I), in which A denotes a radical containing two amino groups, and Z denotes the symbol B or B'; which symbols may be identical or different, and denote a linear or branched alkylene radical which is unsubstituted or substituted by one or more hydroxyl groups or a linear or branched alkylene radical which is unsubstituted or substituted by one or more hydroxyl groups and which contains one or more oxygen, nitrogen and sulphur atoms and 1 to 3 aromatic and/or heterocyclic rings; a polymer of the formula: —A—$Z_1$—A—$Z_1$—(III), in which A is as defined above and each $Z_1$ independently denotes the symbol $B_1$ or $B'_1$ such that it denotes $B'_1$ at least once, $B_1$ being a linear or branched alkylene or hydroxyalkylene radical and $B'_1$ being a linear or branched alkylene radical which is unsubstituted or substituted by one or more hydroxyl radicals and which contains one or more chain nitrogen atoms, the nitrogen atom being substituted by an alkyl chain, an alkyl chain interrupted by an oxygen atom or an alkyl chain interrupted by an oxygen atom which contains one or more hydroxyl groups; an alkylation product of a polymer of the formulae (I) or (II) with an alkyl or benzyl halide or lower alkyl tosylate or mesylate, or an oxidation product of the said polymers, (5) a polyaminopolyamide, (6) a crosslinked polyaminopolyamide which is:

(a) an optionally alkylated, water-soluble crosslinked polyaminopolyamide obtained by crosslinking a polyaminopolyamide prepared by the polycondensation of an acid compound with a polyamine, with a crosslinking agent which is an epihalogenohydrin, diepoxide, dianhydride, unsaturated anhydride or bis-unsaturated derivative, the crosslinking agent being used in an amount from 0.025 to 0.35 mol per amine group of the polyaminoamide;

(b) a water-soluble crosslinked polyaminopolyamide obtained by crosslinking a water soluble polyaminopolyamide with a crosslinking agent which is:

I—a bis-halogenohydrin, bis-azetidinium compound, bis-halogenoacyl-diamine or alkylene dihalide, II—the oligomers obtained by reacting a compound (a) chosen from the group comprising (1) bis-halogenohydrins, (2) bis-azetidinium compounds, (3) bis-halogenoacyl-diamines, (4) bis-(alkyl halides), (5) epihalogenohydrins, (6) diepoxides and (7) bis-unsaturated derivatives, with a compound (b) which is a difunctional compound reactive toward the compound (a); or III—(1) bis-halogenohydrins, (2) bis-azetidinium compounds, (3) bis-halogenoacyl diamines, (4) bis-(alkylhalides), (5) epihalogenohydrins, (6) diepoxides, (7) bis-unsaturated derivatives, and (8) the oligomers obtained by reacting anyone of compounds (1) to (7) with a compound (b) which is a difunctional compound reactive towards compounds (1) to (7); the crosslinking being carried out with 0.025 to 0.35 mol of crosslinking agent per amine group of the polyaminopolyamide, or (c) a polyaminopolyamide derivative resulting from the condensation of a polyalkylenepolyamine with a polycarboxylic acid, followed by alkylation with a difunctional agent;

(7) a polymer obtained by reacting a polyalkylenepolyamine containing two primary amino groups and at least one secondary amino group with a dicarboxylic acid which is diglycolic acid or a saturated aliphatic dicarboxylic acid having 3 to 8 carbon atoms, the molar ratio of the polyalkylenepolyamine to the dicarboxylic acid being from 0.8:1 to 1.4:1, and the resulting polyaminopolyamide being reacted with epichlorohydrin in a molar ratio of epichlorohydrin to the secondary amine groups of the polyaminopolyamide of 0.5:1 to 1.8:1

(8)(a) a cyclic polymer containing chain units corresponding to the formula (III) or (III');

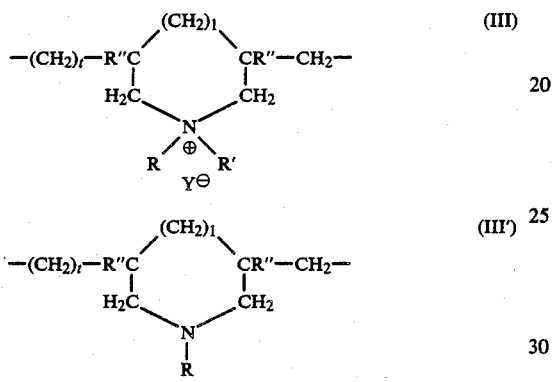

in which l and t are equal to 0 or 1 such that $l+t=1$, R" denotes hydrogen or methyl, R and R' independently of one another denote an alkyl group having from 1 to 22 carbon atoms, a hydroxyalkyl group, or a lower amidoalkyl group, or R and R' denote, together with the nitrogen atom to which they are attached, a heterocyclic group, (b) a copolymer containing units of the formula (III) or (III') and units derived from acrylamide or from diacetoneacrylamide; and $Y^\ominus$ denotes an anion (9) a poly-(quaternary ammonium) compound of the formula:

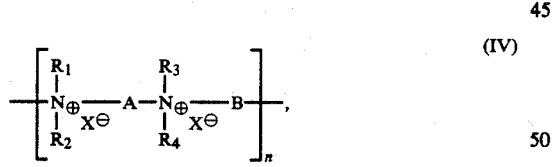

in which $R_1$, and $R_2$, and $R_3$ and $R_4$, which are identical or different, represent an aliphatic, alicyclic or arylaliphatic radical containing at most 20 carbon atoms, or a lower hydroxyaliphatic radical, or $R_1$ and $R_2$, and $R_3$ and $R_4$, together or separately form, with the nitrogen atoms to which they are attached, a heterocyclic ring not containing or containing a second hetero atom other than nitrogen, or $R_1$, $R_2$, $R_3$ and $R_4$ independently represent a group

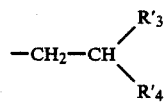

$R'_3$ denoting hydrogen or lower alkyl and $R'_4$ denoting —CN;

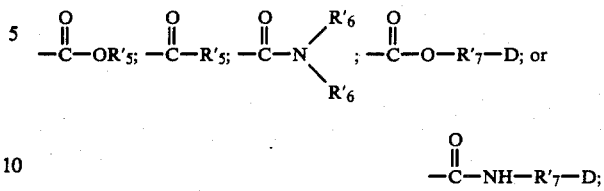

$R'_5$ denoting lower alkyl, $R'_6$ denoting hydrogen or lower alkyl, $R'_7$ denoting alkylene and D denoting a quaternary ammonium group; A and B independently represent an aliphatic group containing from 2 to 20 carbon atoms, which is linear or branched, saturated or unsaturated, and which can contain, in the main chain, one or more groups of the formula:

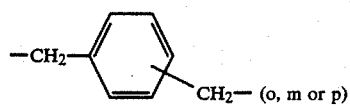

or one or more groups $(CH_2)_n$—Y—$(CH_2)_n$, Y denoting O, S, SO, $SO_2$, —S—S—,

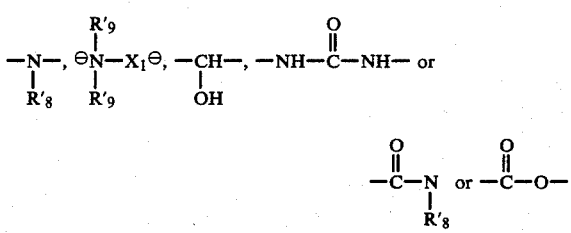

with $X_1^\ominus$ denoting an anion derived from a mineral or organic acid, n being equal to 2 or 3, $R'_8$ denoting hydrogen or lower alkyl and $R'_9$ denoting lower alkyl, or, alternatively, A and $R_1$ and $R_3$ together form a piperazine ring with the two nitrogen atoms to which they are attached; and if A denotes a linear or branched, saturated or unsaturated aliphatic or hydroxyaliphatic radical, B can also denote a group: —$((CH_2))$-$_n$CO—D—OC—$(CH_2)_n$, in which D denotes:

(a) a glycol radical of the formula —O—Z—O—, in which Z denotes a linear or branched hydrocarbon radical or a group corresponding to the formula: —$[CH_2$—$CH_2$—O$]_x$$CH_2$—$CH_2$— or

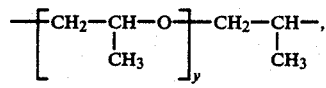

in which X and y denote an integer from 1 to 4,
(b) a bis-secondary diamino radical;
(c) a bis-primary diamino radical of the formula: —NH—Y—NH—, in which Y denotes a linear or branched hydrocarbon radical or a divalent radical —$CH_2$—$CH_2$—S—S—$CH_2$—$CH_2$—; or
(d) a ureylene group of the formula —NH—CO—NH; $X^\ominus$ denotes an anion and n being such that the molecular weight is from 1,000 to 100,000,

(10) a homopolymer or copolymer derived from acrylic or methacrylic acid and containing at least one unit selected from:

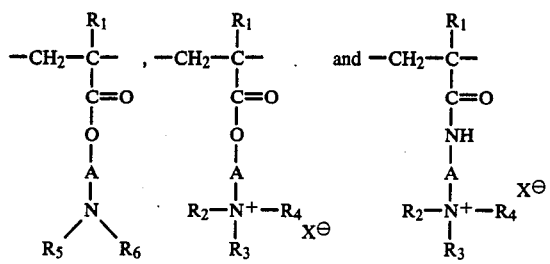

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$, which are identical or different, denote an alkyl group having 1 to 18 carbon atomes or a benzyl group, $R_5$ and $R_6$ independently denote H or alkyl having 1 to 6 carbon atoms, and $X^\ominus$ denotes a methosulphate or halide anion,

(11) a quaternary vinylpyrrolidone/vinylimidazole copolymer,
(12) a polyalkyleneimine,
(13) a polymer containing chain vinylpyridine units or vinylpyridinium units,
(14) a polyamine/epichlorohydrin condensate,
(15) a poly-(quaternary ureylene) compound,
(16) a chitin derivative,
(17) a cationic silicone polymer, or
(18) a cationic derivative of starch or a starch ether.

5. A process according to claim 1 in which the anionic latex is present in an amount from 0.05 to 5% by weight.

6. A process according to claim 1 wherein the cosmetically acceptable medium is in the form of a hair conditioner, a coloring product, bleaching product, shampoo, rinse-off lotion or cream to be applied before or after shampooing, coloring, bleaching, perming or straightening, a setting lotion, a blow-drying lotion, a restructuring lotion, a perming lotion or a straightening lotion.

7. A composition for treating the hair, nails and/or skin, which comprises, in a cosmetically acceptable medium for application to hair, nails and/or skin, about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii), and at least one cationic or amphoteric surface-active agent.

8. A composition according to claim 7 in which the surface-active agent is present in an amount up to 70% by weight of the total weight of the composition.

9. A composition for treating the hair, nails and/or skin, which comprises, in a cosmetically acceptable medium for application to hair, nails and/or skin, about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, about 1.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii), and wherein the cosmetically acceptable medium contains a monoalcohol, polyol, glycol ether or ester thereof or a fatty acid ester of a lower alcohol, in an amount up to 95% by weight.

10. A composition for treating the hair, nails and/or skin, which comprises, in a cosmetically acceptable medium for application to hair, nails and/or skin, about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii), and as an electrolyte, an alkali metal or alkaline earth metal salt of a mineral or organic acid.

11. A composition according to claim 10 in which the salt is present in an amount up to 10% by weight.

12. A process for treating the hair, nails and/or skin, which comprises, applying to hair, nails and/or skin a costmetically acceptable medium containing about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or alternatively by (iv) the introduction of end groups via a chain transfer reaction in the process (ii), and at least one preservative, sequestering agent, thickener, emulsifying agent, softener or form stabilizer.

13. A composition for treating the hair, nails and/or skin, which comprises, in a cosmetically acceptable medium for application to hair, nails and/or skin, about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii) and wherein the composition is in the form of a cream, emulsion, or gel, or packaged in an aerosol can in the form of a spray or foam.

14. A process for treating hair comprising forming in situ on the hair a hair treating composition by first applying to the hair in a cosmetically acceptable medium about 0.01 to 10% by weight of at least one cationic polymer of the polyamine, polyamino polyamide or poly-(quaternary ammonium) type containing amine or ammonium groups in or joined to the polymer chain, said cationic polymer having a molecular weight of 500 to 3,000,000, and subsequently applying to the hair about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii).

15. A process for treating the hair, nails and/or skin, which comprises, applying to hair, nails and/or skin a cosmetically acceptable medium containing about 0.01 to 10% by weight of at least one cationic polymer of the polyamine, polyamino polamide or poly-(quaternary ammonium) type containing amine or ammonium groups in or joined to the polymer chain, said cationic polymer having a molecular weight of 500 to 3,000,000, about 0.01 to 10% by weight of at least one anionic latex which is in the form of a colloidal suspension of particles of polymers containing anionic functional groups, in an aqueous or organic liquid phase, said anionic functional groups being introduced by (i) the polymerization or copolymerization of anionic monomers, by (ii) combination of an anionic free radical derived from a reaction initiator with one or more monomers, during the initiation of the polymerization of the said monomer(s), by (iii) the juxtaposition of these two processes, or by (iv) the introduction of end groups via a chain transfer reaction in the process (ii) and wherein the composition is an aqueous-alcoholic dispersion, emulsion, thickened lotion or gel.

* * * * *